(12) United States Patent
Miller et al.

(10) Patent No.: US 7,385,094 B2
(45) Date of Patent: Jun. 10, 2008

(54) AZEOTROPE COMPOSITIONS COMPRISING TRIDECAFLUORO-3-HEPTENE AND HYDROGEN FLUORIDE AND USES THEREOF

(75) Inventors: Ralph Newton Miller, Newark, DE (US); Mario Joseph Nappa, Newark, DE (US); Velliyur Nott Mallikarjuna Rao, Wilmington, DE (US); Allen Capron Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/590,455

(22) Filed: Oct. 31, 2006

(65) Prior Publication Data

US 2007/0100176 A1    May 3, 2007

Related U.S. Application Data

(60) Provisional application No. 60/732,088, filed on Nov. 1, 2005.

(51) Int. Cl.
*C07C 17/00* (2006.01)
*C07C 17/38* (2006.01)

(52) U.S. Cl. .................... 570/155; 570/178
(58) Field of Classification Search ............ 570/155, 570/178
See application file for complete search history.

(56) References Cited

U.S. PATENT DOCUMENTS 5,171,902 A    12/1992    Krespan et al.
5,268,122 A    12/1993    Rao et al.
5,918,481 A *  7/1999    Pham et al. .............. 62/631

FOREIGN PATENT DOCUMENTS

WO    WO 99/26907        6/1999
WO    WO 2006/086683 A2  8/2006

OTHER PUBLICATIONS

Szapiro, variation of azeotropic composition with pressure, Zesyty Nauk. Politech. Lodz. Chem. (1958), No. 7, 3-16.*
Schotte, "Collection of Phase Equillbrium Data for Separation Technology", Ind. Eng. Chem. Process Des. Dev. 19 (1980), pp. 432-439.
Null, "Phase Equilibrium in Process Design", Wiley-Interscience Publisher (1970), pp. 124-126.
Walas, "Phase Equilibria in Chemical Engineering—Activity Coefficients", Butterworth Publishers (1985), pp. 165-244.
Petrov et al., "Electrophilic Condensation of 1-Hydroperfluoropropylene and 1-Hydroperfluoro-1-Butene with Fluoroethylenes", Bulletin of the Academy of Sciences of the USSR, vol. 31, No. 7, 1982, pp. 1414-1416.
PCT International Search Report dated Apr. 26, 2007 for International Application No. PCT/US2006/042770.

* cited by examiner

*Primary Examiner*—J. Parsa (57) ABSTRACT

Disclosed herein are azeotrope and near-azeotrope compositions comprising 1,1,1,2,2,4,5,5,6,6,7,7,7-tridecafluoro-3-heptene (HFC-162-13mczy, $CF_3CF_2CH{=}CFCF_2CF_2CF_3$) and 1,1,1,2,2,3,5,5,6,6,7,7,7-tridecafluoro-3-heptene (HFC-162-13mcyz, $CF_3CF_2CF{=}CHCF_2CF_2CF_3$) and hydrogen fluoride (HF) and to azeotrope and near-azeotrope compositions comprising 1,1,1,2,2,3,4,5,5,6,6,7,7,7-tetradecafluoroheptane and hydrogen fluoride (HF). These compositions are useful in processes to produce and purify HFC-162-13mcyz, HFC-162-13mczy and HFC-63-14mee.

32 Claims, 1 Drawing Sheet

AZEOTROPE COMPOSITIONS COMPRISING TRIDECAFLUORO-3-HEPTENE AND HYDROGEN FLUORIDE AND USES THEREOF

BACKGROUND OF THE INVENTION

1. Field of the Invention

Disclosed herein are azeotrope compositions comprising tridecafluoro-3-heptene and hydrogen fluoride. The azeotrope compositions are useful in processes to produce and in processes to purify tridecafluoro-3-heptene.

2. Description of Related Art

Chlorine-containing compounds, such as chlorofluorocarbons (CFCs) are considered to be detrimental to the Earth's ozone layer. Many of the hydrofluorocarbons (HFCs), used to replace CFCs, have been found to contribute to global warming. Therefore, there is a need to identify new compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids. Fluorinated olefins, containing one or more hydrogens in the molecule, are being considered for use in some of the applications, like for example in refrigeration.

BRIEF SUMMARY OF THE INVENTION

One aspect relates to an azeotrope or near-azeotrope composition comprising 1,1,1,2,2,4,5,5,6,6,7,7,7-tridecafluoro-3-heptene (HFC-162-13mczy, $CF_3CF_2CH=CFCF_2CF_3$) and 1,1,1,2,2,3,5,5,6,6,7,7,7-tridecafluoro-3-heptene (HFC-162-13mcyz, $CF_3CF_2CF=CHCF_2CF_3$) and hydrogen fluoride (HF).

A further aspect relates to a process for the separation of Z-HFC-162-13 from 1,1,1,2,2,3,4,5,5,6,6,7,7,7-tetradecafluoroheptane (HFC-63-14mcee) comprising: a) forming a mixture of Z-HFC-162-13, HFC-63-14mcee, and hydrogen fluoride; and b) subjecting said mixture to a distillation step from which is formed a column distillate composition comprising an azeotrope or near-azeotrope composition of hydrogen fluoride and Z-HFC-162-13 essentially free of HFC-63-14mcee.

A further aspect relates to a process for the separation of Z-HFC-162-13 from a mixture comprising an azeotrope or near-azeotrope composition of Z-HFC-162-13 and hydrogen fluoride, said process comprising: a) subjecting said mixture to a first distillation step in which a composition enriched in either (i) hydrogen fluoride or (ii) Z-HFC-162-13 is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

A further aspect relates to a process for the purification of Z-HFC-162-13 from a mixture of Z-HFC-162-13, HFC-63-14mcee, and hydrogen fluoride, said process comprising: a) subjecting said mixture to a first distillation step to form a first distillate comprising an azeotrope or near-azeotrope composition containing Z-HFC-162-13 and hydrogen fluoride and a first bottoms comprising HFC-63-14mcee; b) subjecting said first distillate to a second distillation step from which a composition enriched in either (i) hydrogen fluoride or (ii) Z-HFC-162-13 is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition.

A further aspect relates to a process to produce Z-HFC-162-13 comprising: a) feeding HFC-63-14mcee to a reaction zone for dehydrofluorination to form a reaction product composition comprising Z-HFC-162-13, unreacted HFC-63-14mcee and hydrogen fluoride; b) subjecting said reaction product composition to a first distillation step to form a first distillate composition comprising an azeotrope or near-azeotrope composition containing Z-HFC-162-13 and hydrogen fluoride and a first bottoms composition comprising HFC-63-14mcee; c) subjecting said first distillate composition to a second distillation step from which a composition enriched in either (i) hydrogen fluoride or (ii) Z-HFC-162-13 is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed in a third distillate composition with a third bottoms composition enriched in the same component that was enriched in the second distillate composition.

A further aspect relates to a process for the separation of HFC-63-14mcee from a mixture comprising an azeotrope or near-azeotrope composition of HFC-63-14mcee and hydrogen fluoride, said process comprising: a) subjecting said mixture to a first distillation step in which a composition enriched in either (i) hydrogen fluoride or (ii) HFC-63-14mcee is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed in a second distillate composition with a second bottoms composition enriched in the same component which was enriched in the first distillate composition.

A further aspect relates to an azeotrope or near-azeotrope composition comprising 1,1,1,2,2,3,4,5,5,6,6,7,7,7-tetradecafluoroheptane (HFC-63-14mcee) and hydrogen fluoride.

DETAILED DESCRIPTION OF THE INVENTION

One aspect relates to compositions containing 1,1,1,2,2,4,5,5,6,6,7,7,7-tridecafluoro-3-heptene (HFC-162-13mczy, $CF_3CF_2CH=CFCF_2CF_3$) and 1,1,1,2,2,3,5,5,6,6,7,7,7- tridecafluoro-3-heptene (HFC-162-13mcyz, $CF_3CF_2CF=CHCF_2CF_2CF_3$). HFC-162-13mczy and HFC-162-13mcyz, may each exist as one of two configurational isomers, E or Z. Z-HFC-162-13mczy as used herein refers to a mixture of the isomers, E-HFC-162-13mczy and Z-HFC-162-13mczy wherein the predominant isomer is Z-HFC-162-13mczy. Z-HFC-162-13mcyz as used herein refers to a mixture of the isomers, E-HFC-162-13mcyz and Z-HFC-162-13mcyz wherein the predominant isomer is Z-HFC-162-13mcyz. "Z-HFC-162-13" as used herein refers to a mixture of HFC-162-13mczy and HFC-162-13mcyz, wherein both compounds are present predominantly as the Z isomer. Such mixtures of Z-HFC-162-13mczy and Z-HFC-162-13mcyz may be prepared by methods known in the art, such as those described in U.S. Pat. No. 5,268,122, incorporated herein by reference.

As used herein, predominant isomer is intended to mean that isomer which is present in the composition at a concentration of greater than 50 mole percent, preferably greater than 60 mole percent, more preferably greater than 70 mole percent, even more preferably greater than 80 mole percent, and most preferably greater than 90 mole percent.

Anhydrous hydrogen fluoride (HF) is also included in the compositions disclosed herein and is commercially available.

A further aspect relates to compositions containing 1,1,1,2,2,3,4,5,5,6,6,7,7,7-tetradecafluoroheptane (HFC-63-14mcee, $CF_3CF_2CHFCHFCF_2CF_2CF_3$) which may be prepared by methods known in the art, such as those disclosed in U.S. Pat. No. 5,171,902, incorporated herein by reference.

In considering a process for the dehydrofluorination of HFC-63-14mcee to Z-HFC-162-13 and HF and the isolation of Z-HFC-162-13 from such a process, it has been discovered surprisingly that the hydrofluoroolefin Z-HFC-162-13 forms an azeotrope with HF. Additionally, it has been discovered that the hydrofluorocarbon HFC-63-14mcee forms an azeotrope with HF.

One aspect provides a composition, which comprises Z-HFC-162-13 and an effective amount of hydrogen fluoride (HF) to form an azeotrope composition. By effective amount is meant an amount, which, when combined with Z-HFC-162-13, results in the formation of an azeotrope or near-azeotrope mixture.

A further aspect provides a composition, which comprises HFC-63-14mcee and an effective amount of hydrogen fluoride (HF) to form an azeotrope composition. By effective amount is meant an amount, which, when combined with HFC-63-14mcee, results in the formation of an azeotrope or near-azeotrope mixture. As recognized in the art, an azeotrope or a near-azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near-azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotrope compositions in which during boiling or evaporation, the liquid composition changes to a substantial degree.

Additionally, near-azeotrope compositions exhibit dew point pressure and bubble point pressure with virtually no pressure differential. That is to say that the difference in the dew point pressure and bubble point pressure at a given temperature will be a small value. It may be stated that compositions with a difference in dew point pressure and bubble point pressure of less than or equal to 3 percent (based upon the bubble point pressure) may be considered to be a near-azeotrope.

Accordingly, the essential features of an azeotrope or a near-azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near-azeotrope liquid composition is subjected to boiling at different pressures. Thus, an azeotrope or a near-azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

Compositions may be formed that comprise azeotrope combinations of hydrogen fluoride with Z-HFC-162-13. These include compositions comprising from about 90.3 mole percent to about 98.7 mole percent HF and from about 9.7 mole percent to about 1.3 mole percent Z-HFC-162-13 (which forms an azeotrope boiling at a temperature from between about −20° C. and about 108° C. and at a pressure from between about 2.9 psi (20.0 kPa) and about 225 psi (1551 kPa).

Additionally, near-azeotrope compositions containing HF and Z-HFC-162-13 may also be formed. Such near-azeotrope compositions comprise about 0.8 mole percent to about 9.1 mole percent Z-HFC-162-13 and about 99.2 mole percent to about 90.1 mole percent HF at temperatures ranging from about −10° C. to about 90° C. and at pressures from about 4.6 psi (31.7 kPa) to about 143 psi (986 kPa).

Compositions may also be formed that comprise azeotrope combinations of hydrogen fluoride with HFC-63-14mcee. These include compositions comprising from about 94.7 mole percent to less than 100 mole percent HF and from about 5.3 mole percent to greater than 0 mole percent HFC-63-14mcee (which forms an azeotrope boiling at a temperature from between about 13.5° C. and about 120° C. and at a pressure from between about 11.9 psi (82.0 kPa) and about 264 psi (1820 kPa).

Additionally, near-azeotrope compositions containing HF and HFC-63-14mcee may be formed as well. Such near-azeotrope compositions comprise about 0.7 mole percent to about 5.7 mole percent HFC-63-14mcee and about 99.3 mole percent to about 94.3 mole percent HF at temperatures ranging from about 30° C. to about 120° C. and at pressures from about 21.5 psi (148 kPa) and about 264 psi (1820 kPa).

It should be understood that while an azeotrope or near-azeotrope composition may exist at a particular ratio of the components at given temperatures and pressures, the azeotrope composition may also exist in compositions containing other components.

Compositions may be formed that consist essentially of azeotrope combinations of hydrogen fluoride with Z-HFC-162-13. These include compositions consisting essentially of from about 90.3 mole percent to about 98.7 mole percent HF and from about 9.7 mole percent to about 1.3 mole percent Z-HFC-162-13 (which forms an azeotrope boiling at a temperature from between about −20° C. and about 108° C. and at a pressure from between about 2.9 psi (20.0 kPa) and about 225 psi (1551 kPa).

Near-azeotrope compositions may also be formed that consist essentially of about 0.8 mole percent to about 9.1 mole percent Z-HFC-162-13 and about 99.2 mole percent to about 90.9 mole percent HF at temperatures ranging from about −10° C. to about 90° C. and at pressures from about 4.6 psi (31.7 kPa) to about 143 psi (986 kPa).

Compositions may also be formed that comprise azeotrope combinations of hydrogen fluoride with HFC-63-14mcee. These include compositions comprising from about 94.7 mole percent to less than 100 mole percent HF and from about 5.3 mole percent to greater than 0 mole percent HFC-63-14mcee (which forms an azeotrope boiling at a temperature from between about 13.5° C. and about 120° C. and at a pressure from between about 11.9 psi (82.0 kPa) and about 264 psi (1820 kPa).

Additionally, near-azeotrope compositions containing HF and HFC-63-14mcee may be formed as well. Such near-azeotrope compositions comprise about 0.7 mole percent to about 5.7 mole percent HFC-63-14mcee and about 99.3 mole percent to about 94.3 mole percent HF at temperatures ranging from about 30° C. to about 120° C. and at pressures from about 21.5 psi (148 kPa) and about 264 psi (1820 kPa).

It should be understood that while an azeotrope or near-azeotrope composition may exist at a particular ratio of the components at given temperatures and pressures, the azeotrope composition may also exist in compositions containing other components. These additional components include the individual components of the azeotrope composition, said components being present as an excess above the amount being present as the azeotrope composition. For instance, the azeotrope of Z-HFC-162-13 and HF may be present in a composition that has an excess of Z-HFC-162-13, meaning that the azeotrope composition is present and additional Z-HFC-162-13 is also present. Additionally, the azeotrope of HFC-63-14mcee and HF may be present in a composition that has an excess of HFC-63-14mcee, meaning that the azeotrope composition is present and additional HFC-63-14mcee is also present.

Compositions may be formed that consist essentially of azeotrope combinations of hydrogen fluoride with Z-HFC-162-13. These include compositions consisting essentially of from about 90.3 mole percent to about 98.7 mole percent HF and from about 9.7 mole percent to about 1.3 mole percent Z-HFC-162-13 (which forms an azeotrope boiling at a temperature from between about −20° C. and about 108° C. and at a pressure from between about 2.9 psi (20.0 kPa) and about 225 psi (1551 kPa).

Near-azeotrope compositions may also be formed that consist essentially of about 0.8 mole percent to about 9.1 mole percent Z-HFC-162-13 and about 99.2 mole percent to about 90.9 mole percent HF at temperatures ranging from about −10° C. to about 90° C. and at pressures from about 4.6 psi (31.7 kPa) to about 143 psi (986 kPa).

At atmospheric pressure, the boiling points of hydrofluoric acid and Z-HFC-162-13 are about 19.5° C. and 29° C., respectively. The relative volatility at 16.3 psi (112 kPa) and 19.9° C. of HF and Z-HFC-162-13 was found to be nearly 1.0 as 96.7 mole percent HF and 3.3 mole percent Z-HFC-162-13 was approached. The relative volatility at 82.2 psi (567 kPa) and 69.6° C. was found to be nearly 1.0 as 93.1 mole percent HF and 6.9 mole percent Z-HFC-162-13 was approached. These data indicate that the use of conventional distillation procedures will not result in the separation of a substantially pure compound because of the low value of relative volatility of the compounds.

To determine the relative volatility of HF with Z-HFC-162-13, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", $4^{th}$ Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and Z-HFC-162-13 behave in an ideal manner, and can sufficiently predict the relative volatilities of the components in such mixtures. Thus, the relative volatility becomes nearly 1.0 as 3.3 mole percent Z-HFC-162-13 was approached at 19.9° C. This would make it impossible to separate Z-HFC-162-13 from HF by conventional distillation from such a mixture. Where the relative volatility approaches 1.0 defines the system as forming a near-azeotrope or azeotrope composition.

It has been found that azeotropes of Z-HFC-162-13 and HF are formed at a variety of temperatures and pressures. Azeotrope compositions may be formed between 2.9 psi (20.0 kPa) (at a temperature of −20° C.) and about 225 psi (1551 kPa) (at a temperature of 100° C.) said compositions consisting essentially of Z-HFC-162-13 and HF range from about 90.3 mole percent HF (and 9.7 mole percent Z-HFC-162-13) to about 98.7 mole percent HF (and 1.3 mole percent Z-HFC-162-13). An azeotrope of HF and Z-HFC-162-13 has been found at 19.9° C. and 16.3 psi (112 kPa) consisting essentially of about 96.7 mole percent HF and about 3.3 mole percent Z-HFC-162-13. An azeotrope of HF and Z-HFC-162-13 has also been found at 69.6° C. and 82.2 psi (567 kPa) consisting essentially of about 93.1 mole percent HF and about 6.9 mole percent Z-HFC-162-13. Based upon the above findings, azeotrope compositions at other temperatures and pressures may be calculated. It has been calculated that an azeotrope composition of about 98.7 mole percent HF and about 1.3 mole percent Z-HFC-162-13 can be formed at −20° C. and 2.9 psi (20.0 kPa) and an azeotrope composition of about 90.3 mole percent HF and about 9.7 mole percent Z-HFC-162-13 can be formed at 108° C. and 225 psi (1551 kPa). Accordingly, one aspect provides an azeotrope composition consisting essentially of from about 90.3 mole percent to about 98.7 mole percent HF and from about 9.7 mole percent to about 1.3 mole percent Z-HFC-162-13, said composition having a boiling point of about −20° C. at 2.9 psi (20.0 kPa) to about 108° C. at 225 psi (1551 kPa).

It has also been found that azeotrope or near-azeotrope compositions may be formed between about 11.9 psi (82.0 kPa) to about 264 psi (1820 kPa) at temperatures ranging from about 13.5° C. to about 120° C., said compositions consisting essentially of greater than 0 mole percent to about 5.7 mole percent HFC-63-14 mcee and from less than 100 mole percent to about 94.3 mole percent HF.

Compositions may be formed that consist essentially of azeotrope combinations of hydrogen fluoride with HFC-63-14mcee. These include compositions consisting essentially of from about 94.7 mole percent to less than 100 mole percent HF and from about 5.3 mole percent to greater than 0 mole percent HFC-63-14mcee (which forms an azeotrope boiling at a temperature from between about 13.5° C. and about 120° C. and at a pressure from between about 11.9 psi (20.7 kPa) to about 264 psi (1820 kPa).

Near-azeotrope compositions may also be formed that consist essentially of about 94.7 mole percent to less than 100 mole percent HF and from about 5.3 mole percent to greater than 0 mole percent HFC-63-14mcee (which forms an azeotrope boiling at a temperature from between about 13.5° C. and about 120° C. and at a pressure from between about 11.9 psi (20.7 kPa) to about 264 psi (1820 kPa).

At atmospheric pressure, the boiling points of hydrofluoric acid and HFC-63-14mcee are about 19.5° C. and 94.7° C., respectively. The relative volatility at 22 psi (152 kPa) and 30.8° C. of HF and HFC-63-14mcee was found to be nearly 1.0 as 98.5 mole percent HF and 1.5 mole percent HFC-63-14mcee was approached. The relative volatility at 99.6 psi (687 kPa) and 80.2° C. was found to be nearly 1.0 as 96.3 mole percent HF and 3.7 mole percent HFC-63-14mcee was approached. These data indicate that the use of conventional distillation procedures will not result in the separation of a substantially pure compound because of the low value of relative volatility of the compounds.

The "Ptx Method" was also used to determine the relative volatility of HF with HFC-63-14mcee. These measurements were then reduced to equilibrium vapor and liquid compositions in the cell by an activity coefficient equation model, the Non-Random, Two-Liquid (NRTL) equation was also used in this case, to represent liquid phase non-idealities.

Without wishing to be bound by any theory or explanation, it is believed that the NRTL equation can sufficiently predict whether or not mixtures of HF and HFC-63-14mcee behave in an ideal manner, and can sufficiently predict the relative volatilities of the components in such mixtures. It has been found that the relative volatility becomes nearly 1.0 as 1.5 mole percent Z-HFC-162-13 was approached at 30.8° C. This would make it impossible to separate Z-HFC-162-13 from HF by conventional distillation from such a mixture. Where the relative volatility approaches 1.0 defines the system as forming a near-azeotrope or azeotrope composition.

It has been found that azeotropes of HFC-63-14mcee and HF are formed at a variety of temperatures and pressures. Azeotrope compositions may be formed between 11.9 psi (82.0 kPa) (at a temperature of 13.5° C.) and about 264 psi (1820 kPa) (at a temperature of 120° C.) said compositions consisting essentially of HFC-63-14mcee and HF ranging from about 94.7 mole percent HF (and 5.3 mole percent HFC-63-14mcee) to less than 100 mole percent HF (and greater than 0 mole percent HFC-63-14mcee). An azeotrope of HF and HFC-63-14mcee has been found at 30.8° C. and 22 psi (153 kPa) consisting essentially of about 98.5 mole percent HF and about 1.5 mole percent HFC-63-14mcee. An azeotrope of HF and HFC-63-14mcee has also been found at 80.2° C. and 99.6 psi (687 kPa) consisting essentially of about 96.3 mole percent HF and about 3.7 mole percent HFC-63-14mcee. Based upon the above findings, azeotrope compositions at other temperatures and pressures may be calculated. It has been calculated that an azeotrope composition of nearly 100 mole percent HF and about 0.003 mole percent HFC-63-14mcee can be formed at 13.5° C. and 11.9 psi (82.0 kPa) and an azeotrope composition of about 96.3 mole percent HF and about 3.7 mole percent HFC-63-14mcee can be formed at 80.2° C. and 99.6 psi (687 kPa). Accordingly, one aspect provides an azeotrope composition consisting essentially of from about 94.7 mole percent to less than 100 mole percent HF and from about 5.3 mole percent to greater than 0 mole percent HFC-63-14mcee, said composition having a boiling point of about 13.5° C. at 11.9 psi (82.0 kPa) to about 120° C. at 264 psi (1820 kPa).

It has also been found that azeotrope or near-azeotrope compositions may be formed between about 11.9 psi (82.0 kPa) to about 264 psi (1820 kPa) at temperatures ranging from about 13.5° C. to about 120° C., said compositions consisting essentially of greater than 0 mole percent to about 5.3 mole percent HFC-63-14mcee and about less than 100 mole percent to about 94.7 mole percent HF.

The HF/Z-HFC-162-13 azeotrope and near-azeotrope compositions and the HF/HFC-63-14mcee azeotrope and near-azeotrope compositions are useful in processes to produce Z-HFC-162-13, in processes to purify Z-HFC-162-13, and in processes to purify HFC-63-14mcee. In fact, the HF/Z-HFC-162-13 azeotrope and near-azeotrope compositions may be useful in any process that creates a composition containing Z-HFC-162-13 and HF. And HF/HFC-63-14mcee azeotrope and near-azeotrope compositions may be useful in any process that creates a composition containing HFC-63-14mcee and HF.

Azeotropic distillation may be carried out to separate Z-HFC-162-13 from HFC-63-14mcee, which is the starting material for production of Z-HFC-162-13, by vapor phase dehydrofluorination. A two-column azeotropic distillation may then be carried out to separate the co-produced HF from the desired Z-HFC-162-13 product. And another two-column azeotropic distillation may be carried out to separate HF from HFC-63-14mcee. HF may be removed from the halogenated hydrocarbon components of the product mixture using, for example, standard aqueous solution scrubbing techniques. However, the production of substantial amounts of scrubbing discharge can create aqueous waste disposal concerns. Thus, there remains a need for processes utilizing HF from such product mixtures.

While the initial mixture treated in accordance with the processes disclosed herein can be obtained from a variety of sources, including by adding Z-HFC-162-13 to HF-containing compositions, an advantageous use of the present processes resides in treating the effluent mixtures from the preparation of Z-HFC-162-13.

Z-HFC-162-13 may be prepared by the vapor phase dehydrofluorination of HFC-63-14mcee by processes known in the art, such as those described in U.S. Pat. No. 5,268,122, incorporated herein by reference.

A further aspect provides a process for the separation of Z-HFC-162-13 from HFC-63-14mcee comprising: a) forming a mixture of Z-HFC-162-13, HFC-63-14mcee, and hydrogen fluoride; and b) subjecting said mixture to a distillation step from which is formed a column distillate composition comprising an azeotrope or near-azeotrope composition of HF and Z-HFC-162-13 essentially free of HFC-63-14mcee.

As described herein, by "essentially free of HFC-63-14mcee" is meant that the composition contains less than about 100 ppm (mole basis), preferably less than about 10 ppm and most preferably less than about 1 ppm, of HFC-63-14mcee.

This azeotropic distillation takes advantage of the low boiling azeotrope composition formed by Z-HFC-162-13 and HF. The azeotrope composition boils at a temperature lower than the boiling point of either pure component and lower than the boiling point of HFC-63-14mcee as well.

As stated previously, the mixture of Z-HFC-162-13, HFC-63-14mcee and HF may be formed by any practical means. Generally, the present process is particularly useful for the separation of Z-HFC-162-13 from the reaction mixture produced by the dehydrofluorination of HFC-63-14mcee. HF is a co-product formed in this dehydrofluorination reaction. The reaction mixture produced may then be treated by the instant process to remove HFC-63-14mcee. The Z-HFC-162-13 is taken overhead as the distillate from the distillation column as an azeotrope or near-azeotrope composition of Z-HFC-162-13 with HF. The HFC-63-14mcee is taken out of the bottom of the column as a bottoms composition and may contain some amount of Z-HFC-162-13, as well. The amount of Z-HFC-162-13 in the HFC-63-14mcee from the bottom of the distillation column may vary from about 50 mole percent to about 1 part per million (ppm, mole basis) depending on the manner in which the dehydrofluorination reaction is conducted.

The column bottoms composition comprising HFC-63-14mcee and Z-HFC-162-13 may be distilled using, for example, standard distillation techniques to separate the two components. However, it is preferred that the azeotropic distillation be conducted in such a manner as to produce a column bottoms composition comprising HFC-63-14mcee essentially free of Z-HFC-162-13.

In one embodiment, operating the present azeotropic distillation involves modifying the distillation parameters to send not only the Z-HFC-162-13/HF azeotrope overhead, but also send any excess Z-HFC-162-13 overhead as well (this would be Z-HFC-162-13 above the azeotrope concentration). If the appropriate conditions are utilized, then all the Z-HFC-162-13 will go overhead with the HF. Thus, the HFC-63-14mcee removed from the column bottoms will be essentially free of Z-HFC-162-13.

As described herein, by "essentially free of Z-HFC-162-13" is meant that the composition contains less than about 100 ppm (mole basis), preferably less than about 10 ppm and most preferably less than about 1 ppm, of Z-HFC-162-13.

In the distillation step, the distillate exiting the distillation column overhead comprising HF and Z-HFC-162-13 may be condensed using, for example, reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step of the present invention depend upon a number of parameters,. such as the diameter of the distillation column, feed points, and the number of separation stages in the column, among others. The operating pressure of the distillation column may range from about 10 psi pressure to about 200 psi (1380 kPa), normally about 15 psi (103 kPa) to about 50 psi (345 kPa). The distillation column is typically operated at a pressure of about 20 psi (138 kPa) with a bottoms temperature from about 50° C. to about 120° C. and a tops temperature from about 50° C. to about 90° C. Normally, increasing the reflux ratio results in increased distillate stream purity, but generally the reflux ratio ranges between 0.2/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

The column distillate composition comprising an azeotrope or near-azeotrope composition of HF and Z-HFC-162-13, essentially free of HFC-63-14mcee, may be treated to remove the HF and provide pure Z-HFC-162-13 as product. This may be accomplished, for example, by neutralization or by a second distillation process, as described herein.

A further aspect provides a process for the separation of Z-HFC-162-13 from a mixture comprising an azeotrope or near-azeotrope composition of Z-HFC-162-13 and HF, said process comprising: a) subjecting said mixture to a first distillation step in which a composition enriched in either (i) hydrogen fluoride or (ii) Z-HFC-162-13 is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

The process as described above takes advantage of the change in azeotrope composition at different pressures to effectuate the separation of Z-HFC-162-13 and HF. The first distillation step may be carried out at high pressure relative to the second distillation step. At higher pressures, the HF/Z-HFC-162-13 azeotrope contains higher levels of Z-HFC-162-13. Thus, this high-pressure distillation step produces an excess of hydrogen fluoride, which boiling at a higher temperature than the azeotrope will exit the column as the first bottoms composition being pure hydrogen fluoride. The first column distillate is then fed to a second distillation step operating at lower pressure. At the lower pressure, the HF/Z-HFC-162-13 azeotrope shifts to lower concentrations of Z-HFC-162-13. Therefore, in this second distillation step, there exists an excess of Z-HFC-162-13. The excess Z-HFC-162-13, having a boiling point higher than the azeotrope, will exit the second distillation column as the second bottoms composition.

Alternatively, the first distillation step may be carried out at low pressure relative to the second distillation step. At lower pressures, the HF/Z-HFC-162-13 azeotrope contains higher levels of HF. Thus, this low-pressure distillation step produces an excess of Z-HFC-162-13, which boiling at a higher temperature than the azeotrope, will exit the column as the first bottoms composition being pure Z-HFC-162-13. The first column distillate composition is then fed to a second distillation step operating at higher pressure. At the higher pressure, the HF/Z-HFC-162-13 azeotrope shifts to lower concentrations of hydrogen fluoride. Therefore, in this second distillation step there exists an excess of hydrogen fluoride. The excess hydrogen fluoride will exit the second distillation column as the bottoms composition.

The endothermic dehydrofluorination reaction of HFC-63-14mcee to produce Z-HFC-162-13 may be accomplished, for example, in a tubular reactor with catalyst in the tubes and with a heating medium on the shellside of the reactor. Alternatively, a heat carrier may be used to permit adiabatic operation. Either pure HFC-63-14mcee or pure Z-HFC-162-13, both being produced by the distillation processes described herein, may be recycled back to the reactor to serve as heat carrier. HFC-63-14mcee would be a preferred heat carrier, as introduction of Z-HFC-162-13 to the dehydrofluorination reactor will result in a reduction in single-pass conversion of HFC-63-14mcee.

In both the first and second distillation steps, the distillate exiting the distillation column overhead comprising HF and Z-HFC-162-13 may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation steps of the present invention depend upon a number of parameters, such as the diameter of the distillation column, feed points, and the number of separation stages in the column, among others. The operating pressure of the high pressure distillation column (whether high pressure is the first distillation column or the second distillation column) may range from about 50 psi (345 kPa) pressure to about 300 psi (2068 kPa), normally about 100 psi (690 kPa) to about 250 psi (1724 kPa). The high pressure distillation column is typically operated at a pressure of about 225 psi (1551 kPa) with a bottoms temperature of about 117° C. and a tops temperature of about 109° C. Normally, increasing the reflux ratio results in increased distillate stream purity, but generally the reflux ratio ranges between 0.1/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

The operating pressure of the low pressure distillation column (whether low pressure is the first distillation column or the second distillation column) may range from about 5 psi (34 kPa) pressure to about 50 psi (345 kPa), normally about 10 psi (69 kPa) to about 25 psi (172 kPa). The low pressure distillation column is typically operated at a pressure of about 20 psi (138 kPa) with a bottoms temperature of about 85° C. and a tops temperature of about 26° C. Normally, increasing the reflux ratio results in increased distillate stream purity, but generally the reflux ratio ranges between 0.1/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

Figure 1:
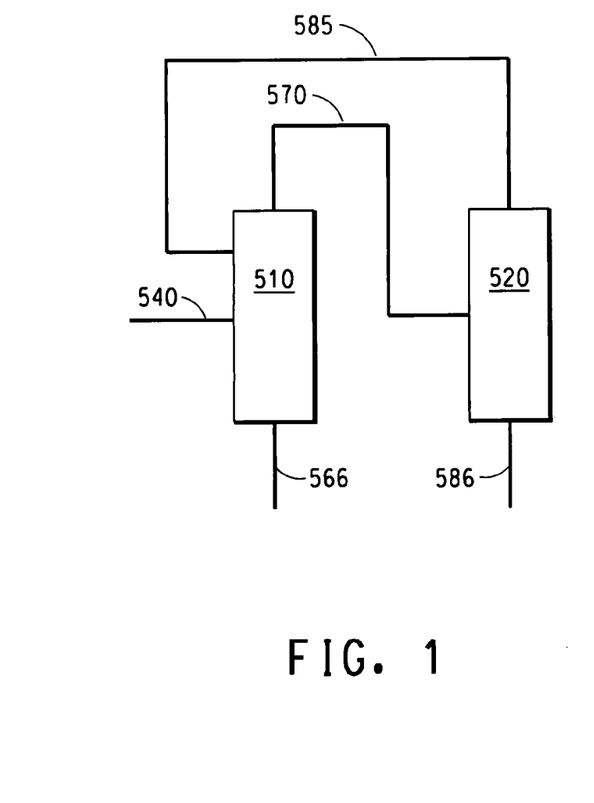
FIG. 1 is a schematic flow diagram illustrating one embodiment for practicing a two-column azeotropic distillation process.

FIG. 1 is illustrative of one embodiment for practicing the present two-column distillation process for the separation of Z-HFC-162-13 and HF. Referring to FIG. 1, a feed mixture derived from a prior azeotropic distillation comprising HF and Z-HFC-162-13, wherein the molar ratio of HF:Z-HFC-162-13 is about 15:1 (or lower), is passed through line (540) to a multiple stage distillation column (510), operating at a temperature of about 25° C. and a pressure of about 20 psi (138 kPa). The bottoms of the distillation column (510), containing essentially pure Z-HFC-162-13 at a temperature of about 85° C. and a pressure of about 22 psi (152 kPa) is removed from the bottom of column (510) through line (566). The distillate from column (510), containing the HF/Z-HFC-162-13 azeotrope (HF:Z-HFC-162-13 molar ratio is about 23:1) at a temperature of about 27° C. and a pressure of about 20 psi (138 kPa) is removed from the top of column (510) and sent through line (570) to a multiple stage distillation column (520). The distillate from column (520), containing the HF/Z-HFC-162-13 azeotrope (molar ratio is about 10:1) at a temperature of about 109° C. and a pressure of about 225 psi (1550 kPa), is removed from column (520) through line (585) and is recycled back to column (510). The bottoms of column (520) containing essentially pure HF at a temperature of about 118° C. and a pressure of about 227 psi (1565 kPa) is removed through line (586).

A further aspect provides a process for the separation of HFC-63-14mcee from a mixture comprising an azeotrope or near-azeotrope composition of HFC-63-14mcee and hydrogen fluoride, said process comprising: a) subjecting said mixture to a first distillation step in which a composition enriched in either (i) hydrogen fluoride or (ii) HFC-63-14mcee is removed as a first distillate composition with a first bottoms composition being enriched in the other of said components (i) or (ii); and b) subjecting said first distillate composition to a second distillation step conducted at a different pressure than the first distillation step in which the component enriched as first bottoms composition in (a) is removed in a second distillate composition with a second bottoms composition enriched in the same component which was enriched in the first distillate composition.

Similar to the previously described two-column azeotropic distillation, for both the first and second distillation steps, the distillate exiting the distillation column overhead comprising HF and HFC-63-14mcee may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step of the present invention depend upon a number of parameters, such as the diameter of the distillation column, feed points, and the number of separation stages in the column, among others. The operating pressure of the high pressure distillation column (whether high pressure is the first distillation column or the second distillation column) may range from about 50 psi (345 kPa) pressure to about 200 psi (1380 kPa), normally about 100 psi (70 kPa) to about 200 psi (1380 kPa). The high pressure distillation column is typically operated at a pressure of about 165 psi (1138 kPa) with a bottoms temperature of about 104° C. and a tops temperature of about 100° C. Normally, increasing the reflux ratio results in increased distillate stream purity, but generally the reflux ratio ranges between 0.1/1 to 50/1. The temperature of the condenser, which is located adjacent to the top of the column, is normally sufficient to substantially fully condense the distillate that is exiting from the top of the column, or is that temperature required to achieve the desired reflux ratio by partial condensation.

The operating pressure of the low pressure distillation column (whether low pressure is the first distillation column or the second distillation column) may range from about 10 psi (69 kPa) pressure to about 100 psi (689 kPa), normally about 15 psi (103 kPa) to about 50 psi (345 kPa). The low pressure distillation column is typically operated at a pressure of about 20 psi (138 kPa) with a bottoms temperature of about 107° C. and a tops temperature of about 28° C. Normally, increasing the reflux ratio results in increased distillate stream purity, but generally the reflux ratio ranges between 0.1/1 to 50/1. The temperature of the condenser, which is located adjacent to the top of the column, is normally sufficient to substantially fully condense the distillate that is exiting from the top of the column, or is that temperature required to achieve the desired reflux ratio by partial condensation.

FIG. 1 is illustrative of one embodiment for practicing the present two-column distillation process for separation of HFC-63-14mcee and HF. Referring to FIG. 1, a feed mixture comprising an azeotrope or near-azeotrope composition of HFC-63-14mcee and HF, wherein the molar ratio of HF:HFC-63-14mcee is about 4.4:1 (or lower), is passed through line (540) to a multiple stage distillation column (510), operating at a temperature of about 27° C. and a pressure of about 20 psi (138 kPa). The bottoms of the distillation column (510), containing essentially pure HFC-63-14mcee at a temperature of about 107° C. and a pressure of about 22 psi (152 kPa) is removed from the bottom of column (510) through line (566). The distillate from column (510), containing the HF/HFC-63-14mcee azeotrope (HF: HFC-63-14mcee molar ratio is about 66:1) at a temperature of about 28° C. and a pressure of about 20 psi (138 kPa) is removed from the top of column (510) and sent through line (570) to a multiple stage distillation column (520). The distillate from column (520), containing the HF/HFC-63-14mcee azeotrope (molar ratio is about 24:1) at a temperature of about 100° C. and a pressure of about 165 psi (1138 kPa), is removed from column (520) through line (585) and is recycled back to column (510). The bottoms of column (520) containing essentially pure hydrogen fluoride at a temperature of about 104° C. and a pressure of about 167 psi (1151 kPa) is removed through line (586).

A further aspect provides a process for the purification of Z-HFC-162-13 from a mixture of Z-HFC-162-13, HFC-63-14mcee, and HF, said process comprising: a) subjecting said mixture to a first distillation step to form a first distillate composition comprising an azeotrope or near-azeotrope composition containing Z-HFC-162-13 and HF and a first bottoms composition comprising HFC-63-14mcee; b) subjecting said first distillate to a second distillation step from which a composition enriched in either (i) hydrogen fluoride or (ii) HFC-63-14mcee is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition.

A further aspect provides a process to produce Z-HFC-162-13 comprising: a) feeding HFC-63-14mcee to a reaction zone for dehydrofluorination to form a reaction product composition comprising Z-HFC-162-13, unreacted HFC-63-14mcee and hydrogen fluoride; b) subjecting said reaction product composition to a first distillation step to form a first distillate composition comprising an azeotrope or near-azeotrope composition containing Z-HFC-162-13 and HF and a first bottoms composition comprising HFC-63-14mcee; c) subjecting said first distillate composition to a second distillation step from which a composition enriched in either (i) hydrogen fluoride or (ii) Z-HFC-162-13 is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition. Optionally, the process may further comprise recycling at least some portion of said first bottoms composition to said reaction zone. Optionally, the process may further comprise recycling at least some portion of said second bottoms composition or said third bottoms composition to said reaction zone. Optionally, the process may further comprise recycling at least some portion of said second bottoms composition or said third bottoms composition to said first distillation step. Optionally, the process may further comprise recovering at least some portion of said second bottoms composition or third bottoms composition as Z-HFC-162-13 essentially free of HFC-63-14mcee and HF.

As described herein, by "essentially free of HFC-63-14mcee and HF" is meant that the composition contains less than about 100 ppm (mole basis), preferably less than about 10 ppm and most preferably less than about 1 ppm, of each of HFC-63-14mcee and HF.

The reaction zone for the dehydrofluorination may comprise a flow reactor preferably containing a fixed bed of dehydrofluorination catalyst. The process equipment for all the processes disclosed herein and the associated feed lines, effluent lines and associated units may be constructed of materials resistant to hydrogen fluoride. Typical materials of construction, well-known to the art, include stainless steels, in particular of the austenitic type, and the well-known high nickel alloys such as Monel® nickel-copper alloys, Hastelloy® nickel based alloys and Inconel® nickel-chromium alloys.

Figure 2:
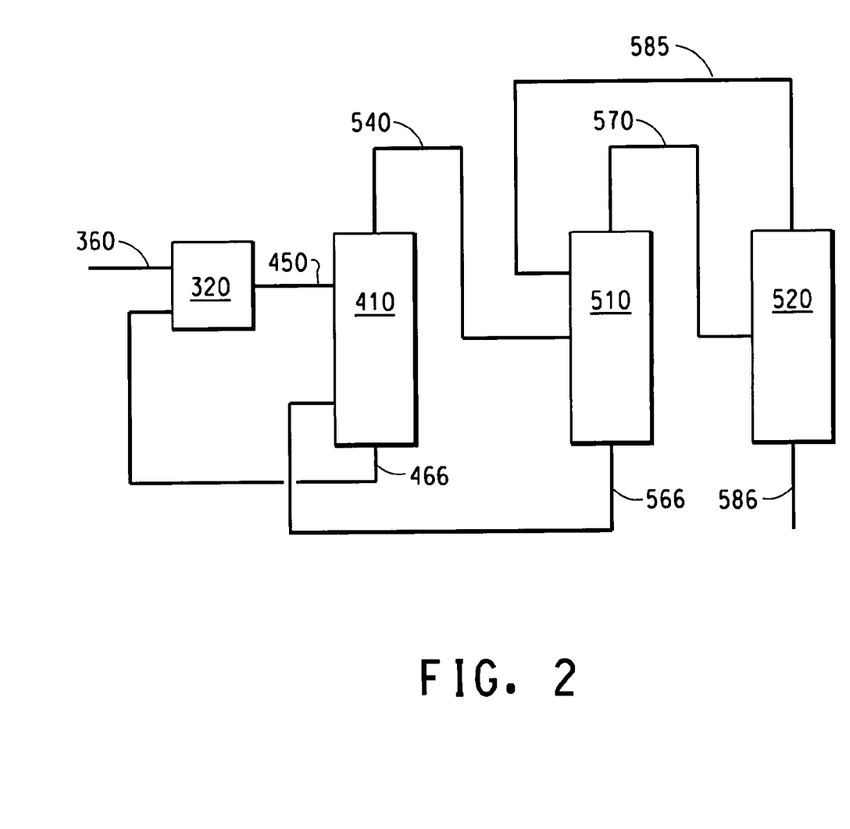
FIG. 2 is a schematic flow diagram illustrating one embodiment for practicing a process for production of Z-HFC-162-13.

FIG. 2 is illustrative of one embodiment for practicing the present process for production of Z-HFC-162-13. HFC-63-14mcee is fed through line (360) to reactor (320). The reactor effluent mixture comprising HF, HFC-63-14mcee and Z-HFC-162-13, exits the reactor through line (450) and is fed to a multiple stage distillation column (410). The bottoms of distillation column (410), containing essentially pure HFC-63-14mcee is removed from the bottom of column (410) through line (466) and may be recycled back to the reactor. The distillate from column (410), containing the HF/Z-HFC-162-13 azeotrope is removed from the top of column (410) and is sent through line (540) to a second multiple stage distillation column (510). The bottoms from column (510), which is essentially pure Z-HFC-162-13, is removed from column (510) through line (566) and may be recycled back to the first distillation column (410). The distillate from column (510), containing the HF/Z-HFC-162-13 azeotrope, is fed through line (570) to a third multiple stage distillation column (520). The distillate from column (520) comprising HF/Z-HFC-162-13 is removed through line (585) and may be recycled to the second distillation column (510). The bottoms composition from column (520) is essentially pure HF and is removed from column (520) through line (586). The essentially pure HF product from this process may be used in any manner appropriate such as feeding to a fluorination reactor for production of a fluorochemical compound, or may be neutralized for disposal.

While not illustrated in the figures, it is understood that certain pieces of process equipment may be used in the processes described herein, for optimization. For instance, pumps, heaters or coolers may be used where appropriate. As an example, it is desirable to have the feed to a distillation column at the same temperature as the point in the column that it is fed. Therefore, heating or cooling of the process stream may be necessary to match the temperature.

Without further elaboration, it is believed that one skilled in the art can, using the description herein, utilize the disclosed compositions and processes to their fullest extent. The following exemplary embodiments are, therefore, to be construed as merely illustrative, and do not constrain the remainder of the disclosure in any way whatsoever.

EXAMPLES

Example 1

Phase Studies of Mixtures of HF and Z-HFC-162-13

A phase study was performed for a composition consisting essentially of Z-HFC-162-13 and HF, wherein the composition was varied and the vapor pressures were measured at both 19.9° C. and 69.6° C. Based upon the data from the phase studies, azeotrope compositions at other temperature and pressures have been calculated.

Table 1 provides a compilation of experimental and calculated azeotrope compositions for HF and Z-HFC-162-13 at specified temperatures and pressures.

TABLE 1

| Temperature, ° C. | Pressure, psi (kPa) | Mole % HF | Mole % Z-HFC-162-13 |
|---|---|---|---|
| −20 | 2.9 (20.0) | 98.7 | 1.3 |
| −15 | 3.7 (25.5) | 98.5 | 1.5 |
| −10 | 4.7 (32.4) | 98.3 | 1.7 |
| −5 | 5.9 (40.7) | 98.1 | 1.9 |
| 0 | 7.3 (50.3) | 97.9 | 2.1 |
| 19.9 | 16.3 (112) | 96.7 | 3.3 |
| 20 | 16.3 (112) | 96.7 | 3.3 |
| 25.1 | 19.7 (136) | 96.4 | 3.6 |
| 40 | 33.2 (229) | 95.4 | 4.6 |
| 60 | 62.3 (430) | 93.9 | 6.1 |
| 65 | 72.1 (497) | 93.5 | 6.5 |
| 69.6 | 82.2 (567) | 93.1 | 6.9 |
| 70 | 83.3 (574) | 93.1 | 6.9 |
| 75 | 95.7 (660) | 92.7 | 7.3 |
| 80 | 110 (758) | 92.3 | 7.7 |
| 85 | 125 (862) | 91.9 | 8.1 |
| 90 | 143 (986) | 91.5 | 8.5 |
| 95 | 162 (1117) | 91.2 | 8.8 |
| 100 | 183 (1262) | 90.8 | 9.2 |
| 108.4 | 225 (1551) | 90.3 | 9.7 |

Example 2

Dew Point and Bubble Point Vapor Pressures for Z-HFC-162-13

The dew point and bubble point vapor pressures for compositions disclosed herein were calculated from measured and calculated thermodynamic properties. The near-azeotrope range is indicated by the minimum and maximum concentration of Z-HFC-162-13 (mole percent, mol %) for which the difference in dew point and bubble point pressures is less than or equal to 3% (based upon bubble point pressure). The results are summarized in Table 2.

TABLE 2

| Temperature, ° C. | Azeotrope composition, mol % Z-HFC-162-13 | Near-azeotrope compositions, mol % Z-HFC-162-13 | |
|---|---|---|---|
| | | Minimum | Maximum |
| −10 | 1.7 | 0.8 | 1.7 |
| 20 | 3.3 | 2.0 | 3.4 |
| 60 | 6.2 | 4.8 | 6.6 |
| 90 | 8.5 | 7.0 | 9.1 |

Example 3

Phase Studies of Mixtures of HF and HFC-63-14mcee

A phase study was performed for a composition consisting essentially of HFC-63-14mcee and HF, wherein the composition was varied and the vapor pressures were measured at both 30.8° C. and 80.2° C. Based upon the data from the phase studies, azeotrope compositions at other temperature and pressures have been calculated.

Table 3 provides a compilation of experimental and calculated azeotrope compositions for HF and HFC-63-14mcee at specified temperatures and pressures.

TABLE 3

| Temperature, ° C. | Pressure, psi (kPa) | Mole % HF | Mole % HFC-63-14mcee |
|---|---|---|---|
| 13.5 | 11.9 (82.0) | <100 | 0.003 |
| 14 | 12.1 (83.4) | 99.9 | 0.1 |
| 14.5 | 12.3 (84.8) | 99.9 | 0.1 |
| 15 | 12.6 (86.9) | 99.8 | 0.2 |
| 20 | 15.1 (104) | 99.3 | 0.7 |
| 25 | 18.1 (125) | 98.8 | 1.2 |
| 27.4 | 19.7 (136) | 98.6 | 1.4 |
| 30 | 21.6 (149) | 98.5 | 1.5 |
| 30.8 | 22.2 (153) | 98.5 | 1.5 |
| 40 | 30.3 (209) | 98.2 | 1.8 |
| 50 | 41.7 (288) | 97.7 | 2.3 |
| 60 | 56.5 (390) | 97.3 | 2.7 |
| 70 | 75.3 (519) | 96.8 | 3.2 |
| 80 | 99.1 (683) | 96.3 | 3.7 |
| 80.2 | 99.6 (687) | 96.3 | 3.7 |
| 90 | 129 (889) | 95.8 | 4.2 |
| 99.8 | 165 (1138) | 95.4 | 4.6 |
| 100 | 165 (1138) | 95.4 | 4.6 |
| 110 | 210 (1484) | 95.0 | 5.0 |
| 120 | 264 (1820) | 94.7 | 5.3 |

Example 4

Dew Point and Bubble Point Vapor Pressures For HFC-63-14mcee

The dew point and bubble point vapor pressures for compositions disclosed herein were calculated from measured and calculated thermodynamic properties. The near-azeotrope range is indicated by the minimum and maximum concentration of HFC-63-14mcee (mole percent, mol %) for which the difference in dew point and bubble point pressures is less than or equal to 3% (based upon bubble point pressure). The results are summarized in Table 4.

TABLE 4

| Temperature, °C. | Azeotrope composition, mol % HFC-63-14mcee | Near-azeotrope compositions, mol % HFC-63-14mcee | |
|---|---|---|---|
| | | Minimum | Maximum |
| 30 | 1.5 | 0.7 | 1.5 |
| 60 | 2.7 | 1.1 | 2.9 |
| 90 | 4.2 | 2.5 | 4.4 |
| 120 | 5.3 | 3.6 | 5.7 |

Example 5

Azeotropic Distillation for Separation of Z-HFC-162-13 From HFC-63-14mcee

A mixture of HF, Z-HFC-162-13, and HFC-63-14mcee is fed to a distillation column for the purpose of purification of Z-HFC-162-13. The data in Table 5 were obtained by calculation using measured and calculated thermodynamic properties.

TABLE 5

| Component or variable | Column feed | Column overhead (distillate) | Column bottoms |
|---|---|---|---|
| HFC-63-14mcee, mol % | 33.4 | 1 ppm | 51.0 |
| Z-HFC-162-13, mol % | 33.3 | 3.6 | 49.0 |
| HF, mol % | 33.3 | 96.4 | — |
| Temp, °C. | — | 58.2 | 93.8 |
| Pressure, psi (kPa) | — | 19.7 (136) | 21.7 (150) |

Example 6

Azeotropic Distillation For Separation of Z-HFC-162-13 from HFC-63-14mcee

A mixture of HF, Z-HFC-162-13, and HFC-63-14mcee is fed to a distillation column for the purpose of purification of Z-HFC-162-13. The data in Table 6 were obtained by calculation using measured and calculated thermodynamic properties.

TABLE 6

| Component or variable | Column feed | Column overhead (distillate) | Column bottoms |
|---|---|---|---|
| HFC-63-14mcee, mol % | 33.4 | 1 ppm | 100 |
| Z-HFC-162-13, mol % | 33.3 | 50.0 | 8 ppm |
| HF, mol % | 33.3 | 50.0 | — |
| Temp, °C. | — | 75.4 | 107 |
| Pressure, psi (kPa) | — | 19.7 (136) | 21.7 (150) |

Example 7

Two-column Azeotropic Distillation For Separation of Z-HFC-162-13 from HF

A mixture of HF and Z-HFC-162-13 is fed to a distillation process for the purpose of purification of the Z-HFC-162-13. The data in Table 7 were obtained by calculation using measured and calculated thermodynamic properties. The numbers at the top of the columns refer to FIG. 1.

TABLE 7

| Compound or variable | 540 Feed Mixture | 570 Column (510) distillate | 566 Z-HFC-162-13 product | 585 Column (520) distillate | 586 HF product |
|---|---|---|---|---|---|
| HF, mol % | 93.9 | 95.8 | 100 | 91.0 | 100 |
| Z-HFC-162-13, mol % | 6.1 | 4.2 | — | 9.0 | — |
| Temp., °C. | — | 26.9 | 84.8 | 109 | 117.5 |
| Pres., psi (kPa) | — | 19.7 (136) | 21.7 (150) | 224.7 (1549) | 226.7 (1563) |

Example 8

Two-column Azeotropic Distillation For Separation of Z-HFC-162-13 from HF

A mixture of HF and Z-HFC-162-13 is fed to a distillation process for the purpose of purification of the Z-HFC-162-13. The data in Table 8 were obtained by calculation using measured and calculated thermodynamic properties. The numbers at the top of the columns refer to FIG. 1.

TABLE 8

| Compound or variable | 540 Feed Mixture | 570 Column (510) distillate | 566 Z-HFC-162-13 product | 585 Column (520) distillate | 586 HF product |
|---|---|---|---|---|---|
| HF, mol % | 61.7 | 96.0 | — | 91.0 | 100 |
| Z-HFC-162-13, mol % | 38.3 | 4.0 | 100 | 9.0 | — |
| Temp., °C. | — | 26.3 | 84.8 | 109 | 117.5 |
| Pres., psi (kPa) | — | 19.7 (136) | 21.7 (150) | 224.7 (1549) | 226.7 (1563) |

Example 9

Two-column Azeotropic Distillation For Separation of HFC-63-14mcee from HF

A mixture of HF and HFC-63-14mcee is fed to a distillation process for the purpose of purification of the HFC-63-14mcee. The data in Table 9 were obtained by calculation using measured and calculated thermodynamic properties. The numbers at the top of the columns refer to FIG. 1.

TABLE 9

| Compound or variable | 540 Feed Mixture | 570 Column (510) distillate | 566 HF product | 585 Column (520) distillate | 586 HFC-63-14mcee product |
|---|---|---|---|---|---|
| HF, mol % | 81.5 | 98.5 | 100 | 96.0 | 100 |
| HFC-63-14mcee, mol % | 18.5 | 1.5 | — | 4.0 | — |
| Temp., °C. | — | 28.3 | 107.4 | 100.3 | 104.1 |
| Pres., psi (kPa) | — | 19.7 (136) | 21.7 (150) | 164.7 (1136) | 166.7 (1150) |

Example 10

Two-column Azeotropic Distillation For Separation of HFC-63-14mcee from HF

A mixture of HF and HFC-63-14mcee is fed to a distillation process for the purpose of purification of the HFC-63-14mcee. The data in Table 10 were obtained by calculation using measured and calculated thermodynamic properties. The numbers at the top of the columns refer to FIG. 1.

TABLE 10

| Compound or variable | 540 Feed Mixture | 570 Column (510) distillate | 566 Column HFC-63-14mcee product | 585 Column (520) distillate | 586 HF product |
|---|---|---|---|---|---|
| HF, mol % | 34.3 | 98.5 | 100 | 96.0 | 100 |
| HFC-63-14mcee, mol % | 65.7 | 1.5 | — | 4.0 | — |
| Temp., ° C. | — | 28.3 | 107.4 | 100.3 | 104.1 |
| Pres., psi (kPa) | — | 19.7 (136) | 21.7 (150) | 164.7 (1136) | 166.7 (1150) |

What is claimed is:

1. An azeotrope or near-azeotrope composition comprising from about 0.8 mole percent to about 9.1 mole percent Z-HFC-182-13 and hydrogen fluoride, wherein said composition is characterized by a difference between dew point pressure and bubble point pressure that is less than or equal to 3%, based upon bubble point pressure.

2. The azeotrope or near-azeotrope composition of claim 1 wherein said composition comprises from about 0.8 mole percent to about 9.1 mole percent Z-HFC-162-13 and from about 99.2 mole percent tb about 90.1 mole percent hydrogen fluoride.

3. The azeotrope or near-azeotrope composition of claim 1 wherein said composition comprises from about 0.8 mole percent to about 9.1 mole percent Z-HFC-162-13 and from about 99.2 mole percent to about 90.1 mole percent hydrogen fluoride, wherein the vapor pressure is from about 2.9 psi (20.0 kPa) to about 225 psi (1551 kPa) at a temperature of from about −20° C. to about 108° C.

4. The azeotrope or near-azeotrope composition of claim 1 wherein said composition consists essentially of from about 0.8 mole percent to about 9.1 mole percent Z-HFC-162-13 and from about 99.2 mole percent to about 90.1 mole percent hydrogen fluoride, wherein the vapor pressure is from about 2.9 psi (20.0 kPa) to about 225 psi (1551 kPa) at a temperature of from about −20° C. to about 108° C.

5. The azeotrope composition of claim 1 wherein said composition comprises from about 1.3 mole percent to about 9.7 mole percent Z-HFC-162-13 and from about 98.7 mole percent to about 90.3 mole percent hydrogen fluoride, wherein the vapor pressure is from about 2.9 psi (20.0 kPa) to about 225 psi (1551 kPa) at a temperature of from about −20° C. to about 108° C.

6. The azeotrope composition of claim 1 wherein said composition consists essentially of from about 1.3 mole percent to about 9.7 mole percent Z-HFC-162-13 and from about 98.7 mole percent to about 90.3 mole percent hydrogen fluoride, wherein the vapor pressure is from about 2.9 psi (20.0 kPa) to about 225 psi (1551 kPa) at a temperature of from about −20° C. to about 108° C.

7. A process for the separation of Z-HFC-162-13 from HFC-63-14mcee comprising:

(a) forming a mixture of Z-HFC-162-13, HFC-63-14mcee, and hydrogen fluoride; and (b) subjecting said mixture to a distillation step from which is formed a column distillate composition comprising an azeotrope or near-azeotrope composition of hydrogen fluoride and Z-HFC-162-13 essentially free of HFC-63-14 mcee, wherein said column distillate composition is characterized by a difference between dew point pressure and bubble point pressure that is less than or equal to 3%, based upon bubble point pressure.

8. The process of claim 7 wherein said distillation step further forms a column-bottoms composition comprising HFC-63-14 mcee.

9. The process of claim 8 wherein said column-bottoms composition comprises HFC-63-14 mcee essentially free of hydrogen fluoride.

10. The process of claim 7 wherein said mixture of Z-HFC-162-13, HFC-63-14 mcee, and hydrogen fluoride comprises equimolar quantities of each component.

11. The process of claim 7 wherein said mixture of Z-HFC-162-13, HFC-63-14 mcee, and hydrogen fluoride comprises excess Z-HFC-162-13.

12. A process for the separation of Z-HFC-162-13 from a mixture comprising an azeotrope or near-azeotrope composition of Z-HFC-162-13 and hydrogen fluoride, wherein said composition is characterized by a difference between dew point pressure and bubble point pressure that is less than or equal to 3%, based upon bubble point pressure, said process comprising:

a) subjecting said mixture to a first distillation step in which a composition enriched in either (i) hydrogen fluoride or (ii) Z-HFC-162-13 is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed in a second distillate composition with a second bottoms composition enriched in the same component which was enriched in the first distillate composition.

13. The process of claim 12 wherein said first bottoms composition comprises Z-HFC-162-13 essentially free of hydrogen fluoride.

14. The process of claim 12 wherein said second bottoms composition comprises hydrogen fluoride essentially free of Z-HFC-162-13.

15. The process of claim 12 wherein said first distillation step is carried out at a pressure greater than the pressure of the second distillation step.

16. The process of claim 12 wherein said mixture consists essentially of Z-HFC-162-13 in combination with an effective amount of hydrogen fluoride to form an azeotrope or near-azeotrope composition with hydrogen fluoride, said azeotrope or near-azeotrope composition containing from about 0.8 mole percent to about 9.1 mole percent Z-HFC-162-13.

17. A process for the purification of Z-HFC-162-13 from a mixture of Z-HFC-162-13, HFC-63-14 mcee, and hydrogen fluoride, said process comprising:

a) subjecting said mixture to a first distillation step to form a first distillate comprising an azeotrope or near-azeotrope composition containing Z-HFC-162-13 and hydrogen fluoride, wherein said first distillate is characterized by a difference between dew point pressure and bubble point pressure that is less than or equal to 3%, based upon bubble point pressure, and a first bottoms composition comprising HFC-63-14 mcee;

b) subjecting said first distillate to second distillation step from which a composition enriched in either (i) hydrogen fluoride or (ii) Z-HFC-162-13 is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed in a third distillate composition with a third bottoms composition enriched in the same component that was enriched in the second distillate composition.

18. A process to produce Z-HFC-162-13 comprising:

a) feeding HFC-63-14 mcee to a reaction zone for dehydrofluorination to form a reaction product composition comprising Z-HFC-162-13 unreacted HFC-63-14 mcee and hydrogen fluoride;

b) subjecting said reaction product composition to a first distillation step to form a first distillate composition comprising an azeotrope or near-azeotrope composition containing Z-HFC-162-13 and hydrogen fluoride, wherein said first distillate composition is characterized by a difference between dew point pressure and bubble point pressure that is less than or equal to 3%, based upon bubble point pressure, and a first bottoms composition comprising HFC-63-14 mcee;

c) subjecting said first distillate composition to a second distillation step from which a composition enriched in either (i) hydrogen fluoride or (ii) Z-HFC-162-13 is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (C) is removed in a third distillate composition with a third bottoms composition enriched in the same component that was enriched in the second distillate composition.

19. The process of claim 18, further comprising recycling at least some portion of said first bottoms composition to said reaction zone.

20. The process of claim 18, further comprising recycling at least some portion of said second bottoms composition or said third bottoms composition to said reaction zone.

21. The process of claim 18, further comprising recovering at least some portion of said second bottoms composition or said third bottoms composition as Z-HFC-162-13 essentially free of HFC-63-14 mcee and hydrogen fluoride.

22. The process of claim 18, further comprising recycling at least some portion of said second bottoms composition or said third bottoms composition to said first distillation step.

23. A process for the separation of HFC-63-14 mcee from a mixture comprising an azeotrope or nearazeotrope composition of HFC-63-14 mcee and hydrogen fluoride, wherein said composition is characterized by a difference between dew point pressure and bubble point pressure that is less than or equal to 3%, based upon bubble point pressure, said process comprising:

a) subjecting said mixture to a first distillation step in which a composition enriched in either (i) hydrogen fluoride or (ii) HFC-63-14 mcee is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed in a second distillate composition with a second bottoms composition enriched in the same component which was enriched in the first distillate composition.

24. The process of claim 23 wherein said first bottoms composition comprises HFC-63-14 mcee essentially free of hydrogen fluoride.

25. The process of claim 23 wherein said second bottoms composition comprises hydrogen fluoride essentially free of HFC-63-14 mcee.

26. The process of claim 23 wherein said second distillation step is carried out at a pressure greater than the pressure of the first distillation step.

27. An azeotrope or near-azeotrope composition comprising from greater than zero mole percent to about 5.7 mole percent HFC-63-14 mcee and hydrogen fluoride, wherein said composition is characterized by a difference between dew point pressure and bubble point pressure that is less than or equal to 3%, based upon bubble point pressure.

28. The azeotrope or near-azeotrope composition of claim 27 wherein said composition comprises from greater than zero mole percent to about 5.7 mole percent HFC-63-14 mcee and from less than 100 mole percent to about 94.3 mole percent hydrogen fluoride.

29. The azeotrope or near-azeotrope composition of claim 27 wherein said composition comprises from greater than zero mole percent to about 5.7 mole percent HFC-63-14 mcee and from less than 100 mole percent to about 94.3 mole percent hydrogen fluoride, wherein the vapor pressure is from about 11.9 psi (82.0 kPa) to about 264 psi (1820 kPa) at a temperature of from about 13.5° C. to about 120° C.

30. The azeotrope or near-azeotrope composition of claim 27 wherein said composition consists essentially of from greater than zero mole percent to about 5.7 mote percent HFC-63-14 mcee and from less than 100 mole percent to about 94.3 mole percent hydrogen fluoride, wherein the vapor pressure is from about 11.9 psi (82.0 kPa) to about 264 psi (1820 kPa) at a temperature of from about 13.5° C. to about 120° C.

31. The azeotrope composition of claim 27 wherein said composition comprises from greater than zero mole percent to about 5.3 mole percent HFC-63-14 mcee and from less than 100 mole percent to about 94.7 mole percent hydrogen fluoride, wherein the vapor pressure is from about 11.9 psi (82.0 kPa) to about 264 psi (1820 kPa) at a temperature of from about 13.5° C. to about 120° C.

32. The azeotrope composition of claim 27 wherein said composition consists essentially of from greater than zero mole percent to about 5.3 mole percent HFC-63-14 mcee and from about less than 100 mole percent to about 94.7 mole percent hydrogen fluoride, wherein the vapor pressure is from about 11.9 psi (82.0 kPa) to about 264 psi (1820 kpa) at a temperature of from about 13.5° C. to about 120° C.

* * * * *